US00PP35437P2

(12) United States Plant Patent
Shipley et al.

(10) Patent No.: US PP35,437 P2
(45) Date of Patent: Oct. 24, 2023

(54) ***LEUCOPHYLLUM* HYBRID PLANT NAMED 'MICROBURST'**

(50) Latin Name: ***Leucophyllum frutescens* X *candidum***
Varietal Denomination: Microburst

(71) Applicants: Nicholas Benoit Shipley, Tucson, AZ (US); Russ A Buhrow, Tucson, AZ (US)

(72) Inventors: Nicholas Benoit Shipley, Tucson, AZ (US); Russ A Buhrow, Tucson, AZ (US)

( * ) Notice: Subject to any disclaimer, the term of this patent is extended or adjusted under 35 U.S.C. 154(b) by 19 days.

(21) Appl. No.: 17/803,919

(22) Filed: Jan. 20, 2023

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

*Primary Examiner* — Kent L Bell

(57) ABSTRACT

A new and distinct *Leucophyllum frutescens* X *candidum* hybrid plant named 'Microburst' is characterized by a dwarf, rounded, dense growth form; purple, fragrant flowers; as well as the strongest resistance to root rotting diseases known within the genus *Leucophyllum*.

2 Drawing Sheets

Latin name: *Leucophyllum frutescens* X *candidum* 'Microburst'.

Varietal denomination: 'Microburst'.

INTRODUCTION

Shrubs of the genus *Leucophyllum* are commonly called Texas Rangers, simply "Rangers" or barometer plant in English and Cenizo in Mexico. The genus consists of about 12 species native to arid portions of Mexico from Puebla in the south northward to the southern portions of Texas. The various "Rangers" have become popular landscape plants throughout the southwestern United States as well as other areas of the world with similar climates and extending into moister areas successfully so long as the soil has adequate drainage. Seven species of *Leucophyllum* are commonly cultivated, as well as several interspecific hybrid cultivars. The most popularly grown species is *Leucophyllum frutescens*. Several cultivars of this species are grown.

BACKGROUND OF THE INVENTION

The present invention relates to a new and distinct cultivar of *Leucophyllum*. The cultivar originated from an intentional breeding program designed to create new cultivars with improved nursery and landscape performance, as many current *Leucophyllum* cultivars are susceptible to damping off diseases both in the nursery and in the landscape. Cultivars are also being selected for other horticultural characteristics such as mature plant size, density and reduced maintenance costs as well as improvement of flowering characteristics.

SUMMARY OF THE INVENTION

Specifically, *Leucophyllum* hybrid 'Microburst' is a selection from within the $F_2$ generation resulting from hybridization utilizing *Leucophyllum frutescens* 'Green Cloud'

(not patented) as the female parent and *Leucophyllum candidum* 'Thundercloud' (not patented) as the male parent. One of the $F_2$ seedlings exhibited an attractive, dwarf, rounded form with silver leaves and dark purple flowers. In addition, this plant displays resistance to excess moisture previously unseen in the genus with one of the plants enduring 5 days of standing water in midsummer 2021 and 2 days of standing water in 2022 within the trial field near Sahuarita, Ariz. This plant is the object of this application. Among the features that distinguish the new *Leucophyllum* cultivar from all other available and commercial varieties of *Leucophyllum* known to the inventor are the following combination of characteristics: dwarf, rounded, dense growth form; purple, fragrant flowers; as well as the strongest resistance to root rotting diseases known within the genus *Leucophyllum*.

The asexual propagation procedure is as follows: Semi-hardwood cuttings 4-5" long are prepared by removing the lower leaves, then dipping the cleared portion of the cut into a 1:10 solution of DIP'N GRO™. The cuttings are then inserted about one inch into prepared peat trays. The trays are moved to a mist house with mist applied every 20 minutes and temperature maintained between 70-85° F. Rooting is generally complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Leucophyllum* hybrid 'Microburst' growing near Sahuarita or Tucson, Ariz., depicted in color as nearly correct as it is possible to make in a color illustration of the character.

DETAILED PLANT DESCRIPTION

Figure 1:
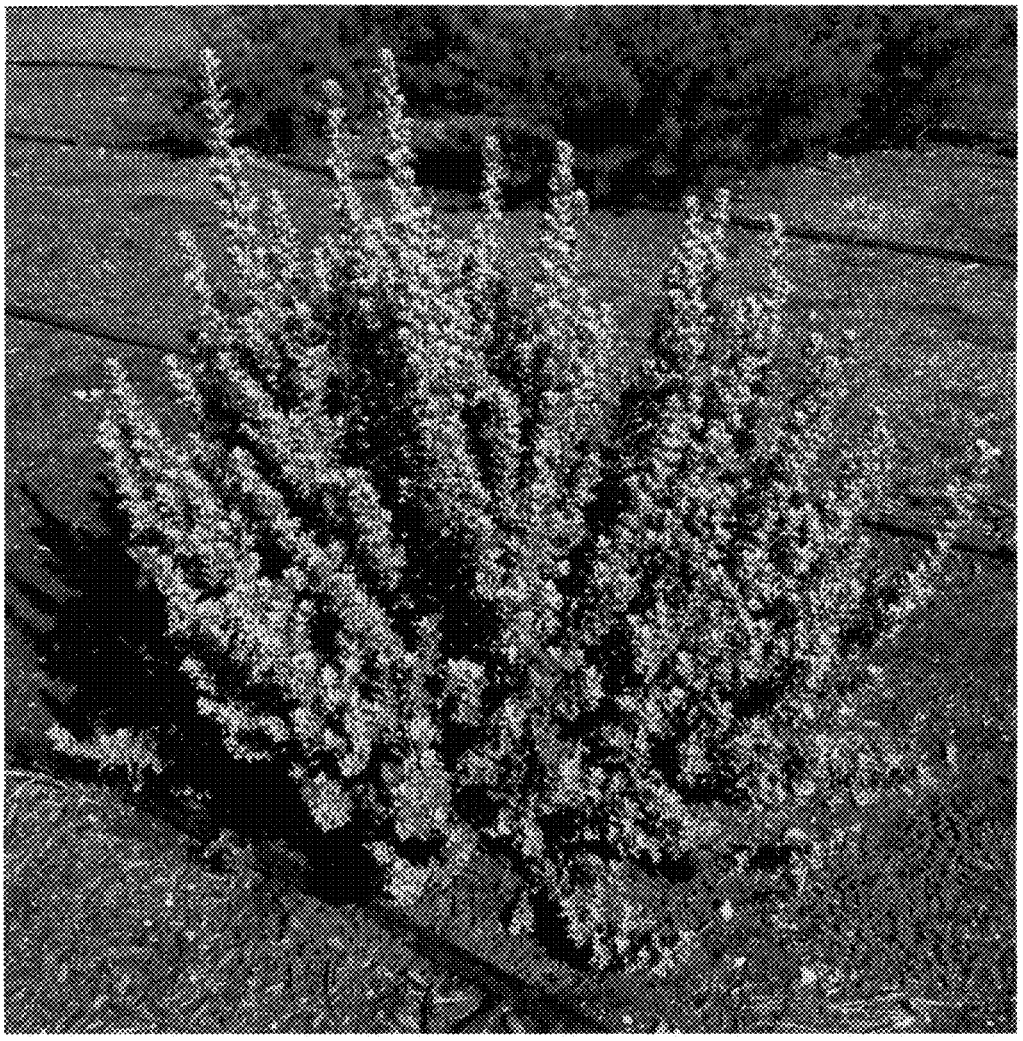
FIG. 1 shows *Leucophyllum frutescens* X *candidum* 'Microburst' aged 2 years growing in a commercial nursery near Sahuarita. Ariz. The plant illustrated tolerated 5 days of standing water in the summer of 2021 with only minor yellowing of the leaves. Photograph from September 2022.
Figure 2:
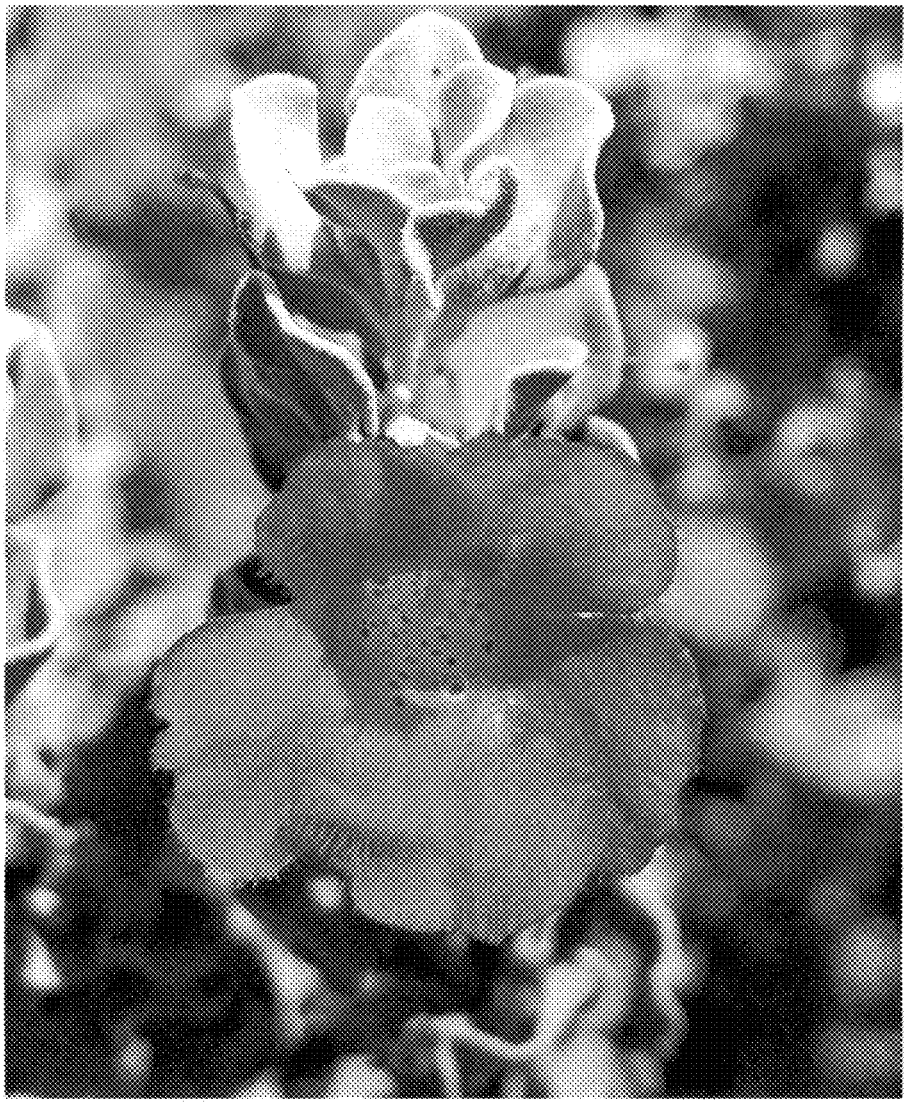
FIG. 2 shows a fresh flower and leaves of *Leucophyllum frutescens* X *candidum* 'Microburst' growing in a nursery container in Tucson, Ariz.

The following is a detailed description of the new *Leucophyllum* hybrid 'Microburst' plant based upon the original plant at age 3 years old growing in the ground near Sahuarita, Ariz. The floral/fruit descriptions are based upon a *Leucophyllum* hybrid 'Microburst' plant growing outdoors in Tucson, Ariz. in a #5 nursery pot. The color descriptions are based upon the 5$^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

'Microburst' is a rounded medium sized shrub measuring about 3.5 feet tall×3.5 feet wide at maturity. No insect or disease problems have been noted with this plant. 'Microburst' is hardy to at least 10° F., USDA zone 7B/8A. 'Microburst' has the highest level of resistance to waterlogging known in the genus *Leucophyllum*. 'Microburst' blooms from April to November at the Sahuarita location. The flowers are single and are produced from the leaf axils, heaviest near the stem apex but also occurring on small lateral branches and throughout the canopy. The flowers have a pleasantly sweet smell and are visited by bees and hummingbirds. Individual flowers last 2-3 days.

Young stems are so densely canescent with plumose stellate hairs that the stem is obscured. These hairs are colored NN155C, the stems 191D. Young stems measure 1.5-2.0 mm in diameter with internode lengths that range from 0.5-7.0 mm. Branch angle varies from 45-60°. Stems at this stage of development are quite soft and flexible. With age the stems become stiff and strong, also losing most of their pubescence, color becoming 177A. At this stage of development stem diameter measures between 2-4 mm. Scaffold branches thicken up to 1cm in diameter, with a glabrous, elongated reticulate surface, the reticulum colored 156D, base without reticulum colored 188B.

Stipules are absent. Axillary buds measure 0.3 mm×0.3 mm and are more or less rounded in shape, canescent, color NN155C. Leaves are alternate, simple, sessile, spatulate, the margin entire except slightly mucronate at the apex. The leaf base is narrowly acute. Leaves measure 7-13 mm long×5-9 mm wide.

The leaf abaxial surface is densely canescent with stellate hairs colored NN155C. The midvein is prominent and visible nearly the full length of the leaf and raised above the general surface. Secondary veins are obscure. The midvein is colored 190B.

The adaxial leaf surface is canescent with stellate hairs colored NN155C. The midvein is visible for ⅗ the length of the leaf and depressed below the general surface. The midvein is colored 190B.

Both leaf surfaces are colored 191A if the light source is 90°, but the color is 191D when the light source is inclined 20° to the leaf surface. As the light angle decreases a gradual color change from 191A to 191B to 191C to 191D occurs, likely due to increased illumination of the leaf hairs relative to the leaf surface below them.

Mature buds are obovoid in shape, 5 angled, the upper 2 petal lobes enclosing the lower 3. Buds measure 15-16 mm in length and 7.5-8.0 mm in diameter. Buds are colored 86B. In bud the corolla exterior is sparsely puberulent with short, straight hairs. The exposed upper petal lobes have ciliate margins, the hairs measure about 0.7 mm in length×30-40μ in diameter, color 86B. Pedicels are terete, canescent with fine, stellate hairs (hair color N155A). Pedicels measure 3 mm in length×0.8-1.0 mm in diameter (color 86B).

The calyx measures 5.3 mm long×5.0 mm wide at the apex, 1.25 mm wide at the base. The calyx is 5 lobed, the lobes lanceolate, free to the receptacle, these measuring 5.0 mm long×1.5 mm wide. The abaxial side of the calyx lobes are mostly appressed to the corolla tube and canescent with stellate hairs colored N155A. The calyx exterior (abaxial side) is less densely pubescent than the pedicel, the hairs thinning from the base to the lobe apex. The calyx is colored 138C but transitions to 86C at the lobe apex. The calyx lobe interior (adaxial surface) is colored 138B, sparsely puberulent with short, straight hairs (colored N155A), which increase in density near the lobe apex about the upper ⅕ of the length of the lobe. The calyx lobe margins are ciliate with short hairs colored N155A.

Flowers are trumpet shaped with 5 petal lobes colored N88B at anthesis but fading to N87B by afternoon in hot weather (95-105° F.). In cooler weather the flowers are colorfast. Flowers measure 25 mm in length while the open end measures 18 mm high×22 mm wide. The upper 2 petal lobes are smaller than the lower 3 and are reflexed. The lower 3 petal lobes are larger and extended. The upper petal lobes are orbicular and ciliate with the interior surface pubescent with straight hairs 0.5-0.6 mm in length colored N88B when the flowers are freshly opened but fading to N87A by afternoon in hot weather. The upper petal lobes measure 6 mm high and 7 mm wide. The petal margin is entire, somewhat crisped (less so with flower age), the apex mucronate. The lower petal lobes are orbicular, entire except for a mucronate apex and somewhat crisped, especially at anthesis. Exterior (abaxial side) petal lobes are colored N87D.

Lower petal lobes measure 9 mm high×9 mm wide adaxially colored N88B at anthesis but fading to N87A by midday in hot weather. The lowest petal lobe is pilose with hairs up to 1 mm long×30-40 μ thick, which are colored N88B at anthesis but fade to N87A by midday. The lateral lower petal lobes are pubescent with straight hairs like those of the lower petal lobe, the pubescence densest on the lower third of these lobes adjacent to the lower petal lobe.

The lower ⅖ of the throat (tube) is bearded with villous hairs up to 1.7 mm long colored N155A. The lower ⅖ of the throat is colored 85B and has scattered round spots measuring 0.3-0.6 mm in diameter which are colored 165B. The upper ⅖ of the tube is glabrous and colored N87B. The middle ⅕ of the tube is transitional between the upper and lower portions.

Stamens 4, epipetalous, attached near the base, incurved and of 2 lengths. Staminode is absent. Anthers explanate, slightly reflexed the medial portion colored 159A, the margins colored N88A. Filaments are terete, glabrous, basally colored 85B and gradually transitioning to NN155D just below the anther attachment. Long stamens measure 12 mm in length and the filament tapers from 0.5 mm diameter at the base to 0.4 mm at the anther attachment. Short stamens measure 8 mm in length and taper from 0.6 mm at the base to 0.4 mm below the anther. Anthers measure 2.7 mm in length×0.8 mm wide×0.3 mm thick.

The pistil is 12 mm long. The ovary is ovoid in shape, glabrous and waxy, color 154D and measures 2 mm long× 1.6 mm in diameter. The style is relatively straight, terete, measuring 0.5 mm thick at the base and 0.4 mm thick near the apex. The style is mostly glabrous and measures 9 mm long up to a fan shaped apex, this portion being 1 mm long×0.9 mm wide×0.4 mm thick. The style is colored 87D. A few straight apically pointing hairs are present at the ovary/style transition, these colored 155A. The stigma follows the outer margin of the fan shaped portion of the style tip and partially hangs below it. The stigma measures 1.4 mm wide×1.3 mm long×0.5 mm thick. The stigma surface is dull, smooth and colored 164C.

Physiologically mature green fruits are ovoid, slightly laterally compressed, basally obtuse, apically obtuse and blunt. The surface is glabrous, shiny waxy, colored 148B. Fruits measure 4.5-5.0 mm long×2.2-2.7 mm wide×1.7-2.7 mm thick.

Ripe, dry fruits, color 165B, are 2 celled capsules that dehisce at the apex along the 2 septum lines and 2 locule lines about 1mm into the fruit from the apex. The fruit surface is dull and waxy. Seeds about 20, all shriveled and inviable, color 202A.

COMPARISONS TO RELATED *LEUCOPHILLUMS*

Compared to its female parent, *Leucophyllum frutescens* 'Green Cloud', 'Microburst' is about ⅓ the size of 'Green Cloud'. The flowers of 'Green Cloud' are colored 64D compared to N88B for those of 'Microburst'. The flowers of 'Microburst' are fragrant while those of 'Green Cloud' are not. 'Green Cloud' is generally considered to be among the most damping off resistant cultivars of *Leucophyllum*. 'Microburst' has damping off resistance exceeding that of 'Green Cloud', tolerating up to 5 days of standing water.

Compared to its male parent *Leucophyllum candidum* 'Thundercloud', 'Microburst' has a rounded form while 'Thundercloud' is about twice as wide as it is tall. 'Thundercloud' flowers are colored 90B and without fragrance while 'Microburst' is colored N88B and fragrant. 'Thundercloud' is among the most susceptible *Leucophyllum* cultivars, so much so that very few nurseries produce it anymore. 'Microburst' has the strongest resistance to damping off known in the genus.

Compared to *Leucophyllum frutescens* 'San Antonio Rose', U.S. Plant Pat. No. 33,454, 'Microburst' is a smaller plant (3.5 feet×3.5 feet compared to 5×5 feet for 'San Antonio Rose'). Flowers of 'San Antonio Rose' measure across the lateral flower face 19-24 mm, color 75A while those of 'Microburst' measure 22 mm wide, color N88B. Floral fragrance of 'Microburst' is slightly stronger than that of 'San Antonio Rose'.

Compared to *Leucophyllum frutescens* 'Convent' (unpatented), 'Microburst' is a smaller plant with a rounded shape while 'Convent' is more upright in growth habit. 'Convent' flowers are colored N74B while those of 'Microburst' are colored N88B. 'Convent' is highly susceptible to damping off diseases, so much so that commercial production of the cultivar is rare. 'Microburst' has the strongest resistance to damping off known within *Leucophyllum.*

Compared to *Leucophyllum frutescens* 'Compacta' (not patented), 'Microburst' is a much smaller plant with flowers colored N88B while those of 'Compacta' are colored 75A. The flowers of 'Compacta' are very weakly fragrant while those of 'Microburst' are noticeably so. Damping off resistance is much stronger in 'Microburst' than that of 'Compacta'.

Compared to 'Heavenly Cloud' (not patented) , an interspecies hybrid between *Leucophyllum frutescens* and *L. laevigatum*, 'Microburst' is less than half as large. 'Microburst' has a rounded form compared to the arching, sprawling form of 'Heavenly Cloud'. 'Microburst' flowers are colored N88B compared to 94C for 'Heavenly Cloud'. Damping off resistance is considerably stronger with 'Microburst'.

Compared to *Leucophyllum frutescens* 'White Cloud' (not patented), 'Microburst' is ⅓ as large. 'White Cloud' has white flowers compared to those of 'Microburst', colored N88B. Damping off resistance is much stronger in 'Microburst'.

Compared to *Leucophyllum* hybrid 'MSWNRascon' (U.S. Plant Pat. No. 33,806P2), 'Microburst' has a rounded form compared to an upright, spreading form for 'MSWNRascon'. The flowers of 'MSWNRascon' are colored 77A, 77B while those of 'Microburst' are colored N88B. The mature size of 'MSWNRascon' was not specified in it's patent so no size comparison is possible.

Compared to *Leucophyllum frutescens* 'GREHJS' (U.S. Plant Pat. No. 33,638P2), 'Microburst' has 5 flower petal lobes colored N88B, while 'GREHJS' has 6 petal lobes of differing colors, the upper ones colored 75A. The growth habit of 'GREHJS' is upright and spreading, while 'Microburst' is rounded.

We claim:

1. A new and distinct *Leucophyllum* hybrid plant named 'Microburst' substantially as described and illustrated herein.

* * * * *